United States Patent [19]

Hartman

[11] Patent Number: 4,940,328

[45] Date of Patent: Jul. 10, 1990

[54] OPTICAL SENSING APPARATUS AND METHOD

[75] Inventor: Nile F. Hartman, Stone Mountain, Ga.

[73] Assignee: Georgia Tech Research Corporation, Atlanta, Ga.

[21] Appl. No.: 267,212

[22] Filed: Nov. 4, 1988

[51] Int. Cl.[5] ............................................. G01B 9/02
[52] U.S. Cl. .................................. 356/345; 350/46.12
[58] Field of Search ............................. 356/345, 354; 350/96.12, 96.13

[56] References Cited

U.S. PATENT DOCUMENTS

| | | | |
|---|---|---|---|
| 3,923,372 | 12/1975 | Dabby et al. | 350/96 |
| 4,447,116 | 5/1984 | King et al. | 350/96.13 |
| 4,515,430 | 5/1985 | Johnson | 350/96.13 |
| 4,536,088 | 8/1985 | Rashleigh et al. | 356/345 X |
| 4,552,457 | 11/1985 | Giallorenzi | 356/345 |
| 4,608,344 | 8/1986 | Carter et al. | 436/34 |
| 4,627,731 | 12/1986 | Waters et al. | 356/349 |

FOREIGN PATENT DOCUMENTS

| | | | |
|---|---|---|---|
| 75231 | 4/1987 | Japan | 356/345 |
| 1320721 | 6/1987 | U.S.S.R. | 356/345 |

OTHER PUBLICATIONS

P. K. Tien, Light Waves in Thin Films and Integrated Optics, Appl. Opt., 10, 11, Nov. 1971.
H. F. Taylor et al., Guided Wave Optics, Proc. of IEEE, 62, 8, Aug. 1974.
R. Ulrich, Efficiency of Optical-Grating Couplers, J. Opt. Soc., 63, 11, Nov. 1973.

*Primary Examiner*—Davis L. Willis
*Assistant Examiner*—Matthew W. Koren
*Attorney, Agent, or Firm*—Martin M. Novack

[57] ABSTRACT

Optical devices and techniques are disclosed for sensing properties of an environment with improved stability and lower cost. In a disclosed embodiment, there is provided a substrate having an index of refraction $n_s$. A waveguide layer is provided and has a surface adjacent the substrate, the waveguide layer having an index of refraction $n_f$ that is greater than $n_s$. A superstrate is provided adjacent the opposing surface of the waveguide layer, the superstrate having an index of refraction $n_c$ that is less than $n_f$, the index of refraction of the superstrate being affected by the environment. An optical beam is injected into the waveguide layer such that at least two modes of the beam propagate in the waveguide layer. The interfering product of said at least two modes of the beam which have propagated through the waveguide layer is then detected.

19 Claims, 4 Drawing Sheets

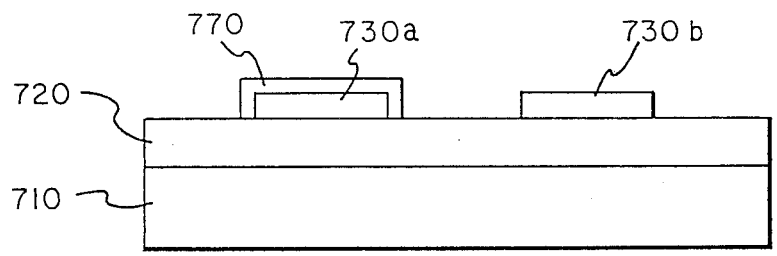
Fig. 7
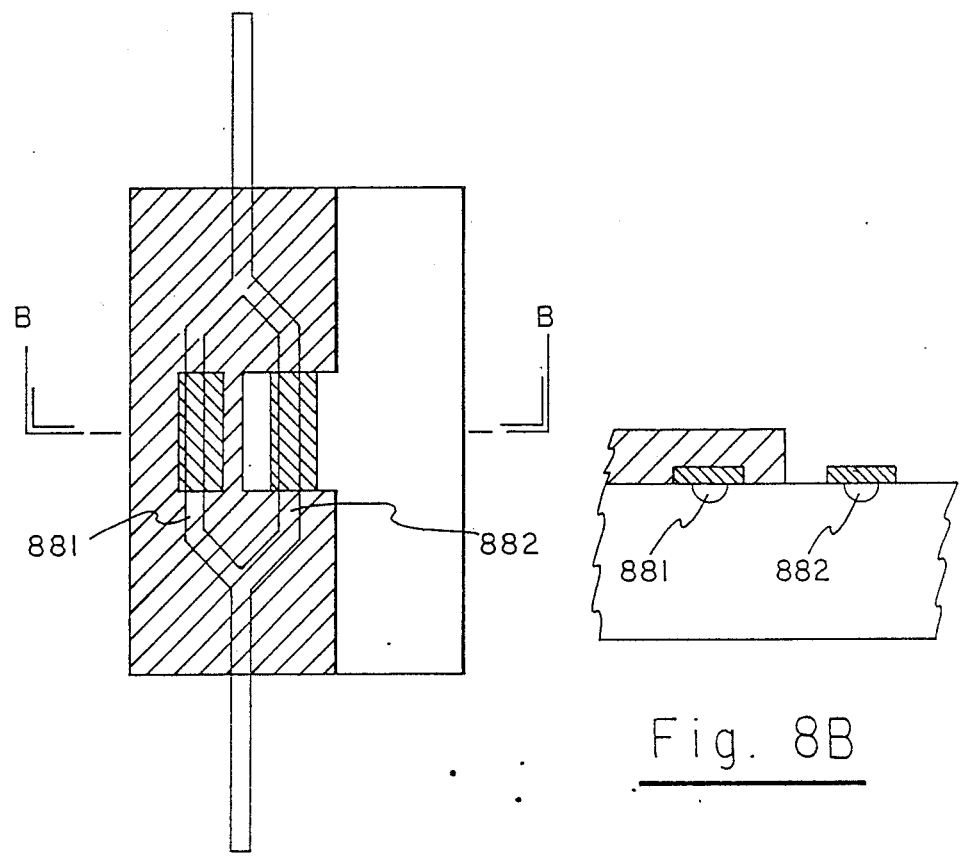
Fig. 8B
Fig. 8A

OPTICAL SENSING APPARATUS AND METHOD

BACKGROUND OF THE INVENTION

The invention relates to optical devices and techniques for sensing properties of an environment, such as the presence of a substance in the environment or the measurement of pressure, magnetic fields or electric fields.

The development of integrated optical devices has evolved in recent years, and these devices have shown promise of providing highly sensitive detectors of substances in an environment, such as chemicals or biological materials. The devices also measure other properties, such as pressure, magnetic fields or electric fields. A class of these devices, which are of interest herein, measure a change in index of refraction caused by the property being measured. The light which is used to determine the change in index of refraction can be carried to and from the device by optical fibers, so the devices can be of a passive nature that is advantageous for many applications, for example monitoring explosive mixtures, flammable materials or toxic substances, etc. The devices can be very small in size and can be put in relatively inaccessible places. The devices are also relatively inexpensive to manufacture in quantity, and a number of them can be utilized together to obtain measurements that are over a wide range of values as well as highly sensitive.

An example of the described type of device is shown in the U.S. Pat. No. 4,515,430 of Johnson which discloses an integrated optical transducer that is stated to include a single mode input optical waveguide formed in a single substrate which divides into optical waveguide branches of different physical lengths, the two branches recombining into a single mode output waveguide. When used as a transducer, the optical path lengths of the waveguide branches are stated to be dependent on a physical quantity to be measured. The patent notes that the transducer can be used as a temperature sensing transducer or may be used to sense other parameters on which either the index of refraction or the length of the waveguide branches are dependent, including pressure, strain, electric or magnetic fields, electromagnetic radiation, or chemical activity.

Notwithstanding the listed potential advantages of previously proposed integrated optical sensors such as the one set forth in the Johnson patent, there are disadvantages which can limit their practical application. Because there are separate optical paths for the respective branches, temperature changes can effect the branches differently, particularly when the branches are of different lengths as specified in the Johnson patent. Therefore, temperature variations can introduce substantial errors when attempting to measure properties such as the presence of a substance, presence of a field, etc. The two arms may also be effected differently by mechanical perturbations. Additionally, the requirement for single mode operation, as in Johnson, renders the device fabrication more difficult and expensive.

It is among the objects of the present invention to overcome the indicated disadvantages of the prior art and to provide improvement in integrated optical sensors.

SUMMARY OF THE INVENTION

The present invention is directed to optical devices and techniques for sensing properties of an environment with improved stability and lower cost.

In accordance with an embodiment of the invention, the method for sensing a property of an environment includes the steps of providing an optical waveguide in the environment and injecting a light beam into the waveguide such that at least two modes of the beam propagate in the waveguide, the effective index of refraction for the modes of the beam being affected by the property to be sensed. A further step of the invention includes generating an electrical signal representative of the interfering product of the at least two modes of the beam which have propagated through the waveguide. The signal is indicative of the property of the environment.

In one preferred form of the method of the invention wherein the method is used to sense a substance in the environment, there is provided an optical waveguide having a boundary with an index of refraction that depends on the substance in the environment that is to be sensed. Again, a light beam is injected into the waveguide such that at least two modes of the beam propagate in the waveguide, and an electrical signal is generated which is representative of the interfering product of the at least two modes of the beam which have propagated through the waveguide, the signal being indicative of the substance. In a form of the invention, a selective coating is provided at the boundary, the coating having an index of refraction that is affected by the substance to be sensed. If desired, a plurality of the coatings can be provided at the boundary, and the coatings can have indices of refraction that are affected by said substance, but with different sensitivities. Alternatively, the coatings can have indices of refraction that are affected by different substances.

In an embodiment of the apparatus of the invention, there is provided a substrate having an index of refraction $n_s$. A waveguide later is provided and has a surface adjacent the substrate, the waveguide layer having an index of refraction $n_f$ that is greater than $n_s$. A superstrate is provided adjacent the opposing surface of the waveguide layer, the superstrate having an index of refraction $n_c$ that is less than $n_f$, the index of refraction of the superstrate being affected by the environment. Means are provided for injecting an optical beam into the waveguide layer such that at least two modes of the beam propagate in the waveguide layer. Means are also provided for detecting the interfering product of said at least two modes of the beam which have propagated through the waveguide layer.

As demonstrated below, the described apparatus and technique provides good sensitivity and also exhibits stability in environment having temperature variations and/or mechanical disturbances. The devices and methods hereof also have the previously described advantages of integrated optical devices which have passive sensors and can be used in difficult environments. The present invention has the added advantage of easier and less expensive fabrication, and can be made smaller than existing devices.

In accordance with a further feature of the invention, there is provided a sensing apparatus which exhibits further temperature stability characteristics. In this embodiment, a pair of optical waveguide sections (which can be individual waveguides or branches of a Mach- Zehnder type of interferomoter arrangement) are disposed in the environment to be monitored. A coating is provided on each of the waveguide sections, each of the coatings having an index of refraction that changes when it is exposed to the substance being monitored. A protective covering is provided on one of the coatings such that one coating is projected from exposure to the environment and the other coating is exposed to the environment. Means are provided for injecting optical beams into the optical waveguide sections, and means responsive to the combined beam outputs are provided for sensing the substance. In a form of this embodiment, the means responsive to the combined beam outputs includes means for substracting the respective outputs of the optical waveguide sections.

Further features and advantages of the invention will become more readily apparent from the following detailed description when taken in conjunction with the accompanying drawings.

BRIEF DESCRIPTION OF THE DRAWINGS

FIG. 7 illustrates a further embodiment of the invention which employs a temperature correction technique in an integrated optical sensing device that has two branches.

FIGS. 8A and 8B (FIG. 8B being a cross-sectional through a section defined by arrows B—B in FIG. 8A) illustrates another form of an embodiment with temperature correction.

DESCRIPTION OF THE PREFERRED EMBODIMENT

Figure 1:
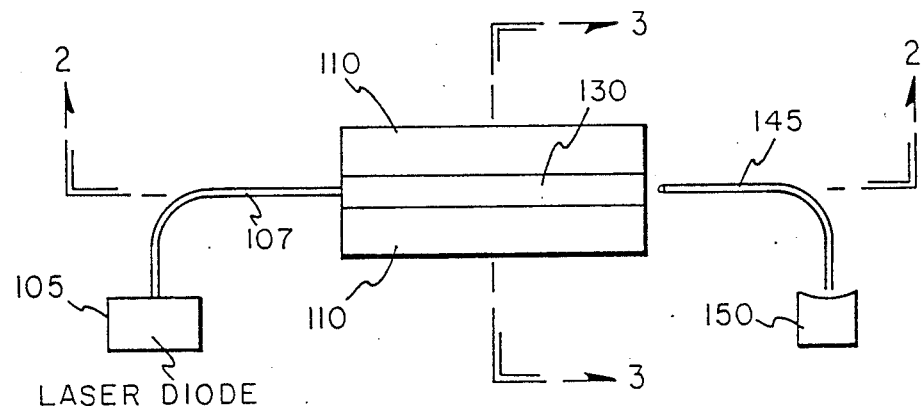
FIG. 1 is a diagram, partially in block form, of an apparatus in accordance with an embodiment of the invention, and which can be used to practice the method of the invention.
Figure 2:
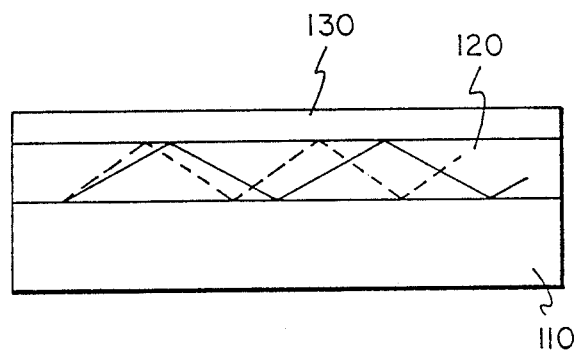
FIG. 2 is a cross-sectional view, as taken through a section defined by arrows 2—2, of a portion of the FIG. 1 embodiment.
Figure 3:
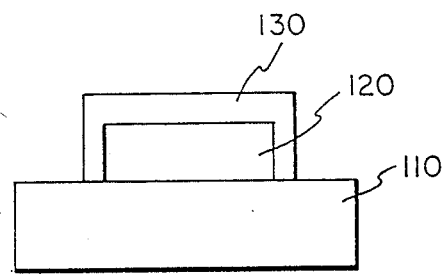
FIG. 3 is a cross-sectional view, as taken through a section defined by arrows 3—3, of a portion of the FIG. 1 embodiment.

Referring to FIG. 1, there is shown a diagram of an apparatus in accordance with an embodiment of the invention and which can be used to practice an embodiment of the method of the invention. A substrate 110 is provided, and has thereon an optical wave guiding layer 120 (see also FIGS. 2 and 3). The substrate may be, for example, a glassy material such as fused silica or a polymer layer. The waveguide layer 120 has a higher index of refraction than the substrate. The waveguide layer may be, for example, another glassy layer or polymer layer. The waveguide layer 120 may be deposited on the substrate, for example by sputtering (for a glassy layer) or by solution deposition (for a polymer layer). Alternatively, the waveguide layer may be formed in the substrate layer, such as by suitable doping of the surface thereof with a dopant that raises the index of refraction of the substrate material. In the present embodiment, a superstrate or cover layer 130 is deposited over the waveguide layer, the superstrate layer having a lower index of refraction than the waveguide layer. The superstrate layer 130 may be, for example, a polymer or an organic dye coating that reacts with a fluid environment (e.g. a gas, a liquid or vapor) in a manner that changes the index of refraction of said superstrate layer. For example, $NH_3$ vapor can be sensed as it increases the index of refraction of an organic dye. It will be understood, however, that the covering medium may be any substance which has a lower index of refraction than the waveguide layer, for example air or another fluid whose properties are to be measured.

Figure 4:
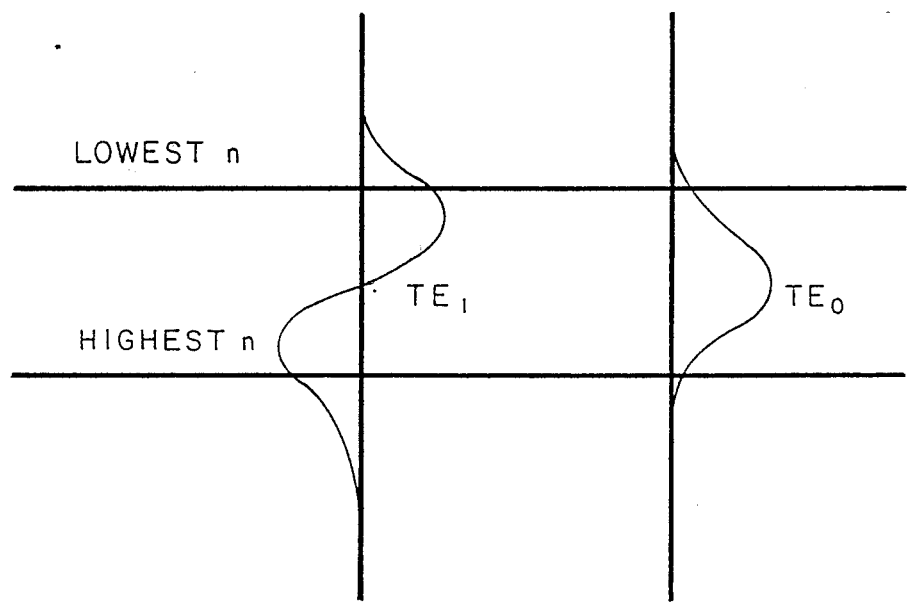
FIG. 4 illustrates the nature of the electric field vector of an optical wave propagating in a waveguide layer.

In the present embodiment, a coherent light source such as a laser diode 105 and an optical fiber 107 are used to inject light into the waveguide layer for propagation therein in at least two modes. The modes which propagate will be determine by the wavelength of the light, the thickness of the waveguide layer, and the indices of refraction of the substrate 110 ($n_s$), the waveguide film 120 ($n_f$) and the superstrate covering layer 130 ($n_c$). Each guided mode exhibits an effective index of refraction, with the lowest order mode characterized by a slightly higher effective refractive index than the next higher order mode. [See, for example, P.K. Tien, "Light Waves In Thin Films And Integrated Optics", Applied Optics, Vol. 10, No. 11 (1971.)] To understand operation of this embodiment of the invention, reference can be made to the diagram of FIG. 2. Consider the interference that will occur between the lowest order mode (solid line) and a higher order mode (dashed line) in the waveguide. Because the higher order mode is closer to cutoff, it is more sensitive to the superstrate. The evanescent field of the lowest order made is not affected as strongly by the superstrate. [In this regard, see FIG. 4, which illustrates the electric fields for the zero order ($TE_o$) and first order ($TE_1$) for propagetion of these modes in a central region of highest index of refraction that is between top and bottom regions of lower index of refraction. The field of the higher order mode extends more into the regions of lower refractive index —see Taylor et al., Proc. IEEE, 62, 1044 (1974).] As a result, its effective mode refractive index changes with variations of the superstrate index. Therefore, by interfering the lowest order waveguide mode with a higher order waveguide mode, very small changes in the superstrate refractive index can be detected. Since the different modes travels in the same waveguide, they see identical temperature effects and mechanical disturbances in the waveguide. The result is an interferometer that is sennsitive but exhibits stability in environments having temperature variations and/or mechanical disturbances.

In the embodiment of FIG. 1, the described interference will result in an output fringe pattern in the form of horizontal bars with sinusoidally varying intensity in the vertical direction. As the index of refraction of the superstrate changes, the pattern will change. The intensity at a point (actually a small region) on the pattern can be observed using an optical fiber 145 (FIG. 1) having an aperture that is preferably small compared to the period of the fringe pattern. The fiber output is coupled of photodetector 150 whose output therefore varies with the refractive index of the superstrate and is accordingly indicative of the environment property being measured. The photodector output can be coupled to a suitable recorder, processor, and/or control circuit (not shown), consistent with the particular application of monitoring and/or control for which that device is being used. [The same is true for other illustrated embodiments.] It will be understood that alternative means for measuring the fringe pattern, such as well known machine vision techniques, can also be employed.

The sensitivity of the described type of device can be illustrated by the following example. In a system wherein the indices of refraction of the substrate and waveguide layers are respectively $n_s = 1.515000$ and $n_f = 1.600000$, the superstrate index of refraction $n_c$ is as indicated below and the waveguide thickness is 5 microns, the 0 order mode (lowest order) was calculated as being interfered with the 6th order mode, and the relative phase change produced by a given change in the superstrate index of refraction was computed. The effective index for the two modes $n_{eff}$(0 order) and $n_{eff}$(6th order) for two different values of superstrate index $n_c$ are as follows:

$n_c = 1.550000$
$n_{eff}$(0 order) = 1.598949
$n_{eff}$(6th order) = 1.550453
$n_c = 1.550010$
$n_{eff}$(0 order) = 1.598949
$n_{eff}$(6th order) = 1.550456

In this example, for a superstrate refractive index difference of $1 \times 10^{-5}$, the effective index for the zero order mode does not change in the first six decimal places, while the effective index for the 6th order mode changes by $3 \times 10^{-6}$. Assuming a free space wavelength of $0.6238 \times 10^{-4}$ cm and a path length of 2 cm, the resulting phase change, $\Delta\phi$, due to the effective index difference between the 6th order modes is 0.18 $\pi$. In the case of an interferometer, the output intensity $I_x$ as a function of phase difference is described by the following equation:

$$I_x = (I_o/2)\ [1 + \cos(\phi + \Delta\phi)]$$

where $I_o$ is the maximum output intensity. For $\Delta\phi = \phi 0.18\ \pi$, $\Delta I_x = 0.26 I_o$ for $\phi = \pi/2$. In practice, phase differences of 0.064 $\pi$ are readily detected, and this corresponds to an index change of the superstrate of only about $5 \times 10^{-6}$. Using active detection techniques, for example phase locked detection, the sensitivity can be increased substantially.

Although the example pertains to interference between two modes, it will be understood that interference between further modes, which also depend on the index of refraction being measured, can be used. Their effects can be determined empirically. Also, the mode selection can be employed in the design (as previously described) or can be modified using appropriate mode selection filtering, as described below.

As above noted, the embodiment set forth has improved temperature stability, but it will be understood that large temperature excursions may cause the loss or addition of new waveguide modes that could affect sensor performance.

Figure 5:
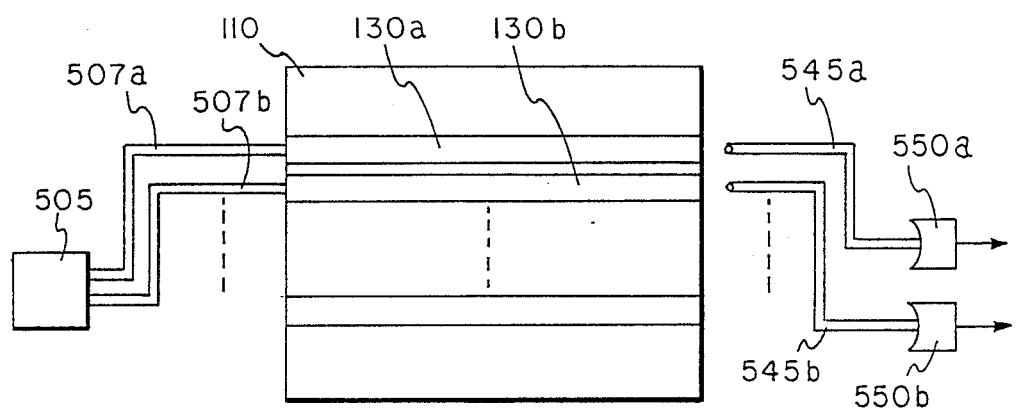
FIG. 5 illustrates a further embodiment of the invention which employs a plurality of sensors.

Referring to FIG. 5, there is shown an embodiment of the invention wherein a plurality of waveguides with respective superstrates 130a and 130b (as in FIG. 1—two of the plurality being labelled) are formed on the same substrate 110. Light is injected from a source such as one or more laser diodes 505 via optical fibers 507a, 507b. Output fibers 545a, 545b and photodetectors 550a, 550b are provided, as previously described, in conjunction with FIG. 1. The superstrates can be, for example, materials that have index of refraction sensitivity to different substances (or properties) or different degrees of sensitivity to the same substance (or property). As before, the photodetector outputs can be recorded and/or processed as desired.

Figure 6:
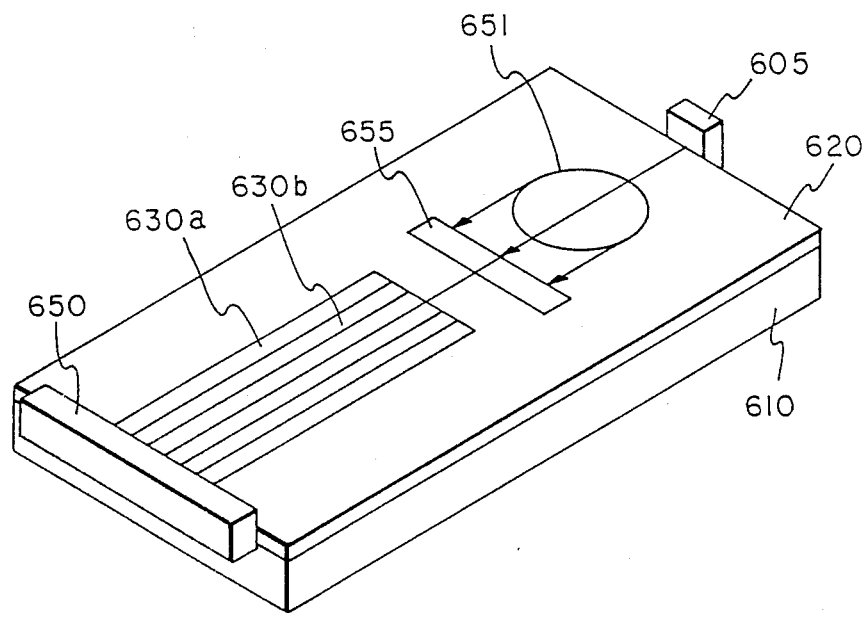
FIG. 6 illustrates another embodiment of the invention which employs a plurality of sensors.

FIG. 6 shows another embodiment which has a plurality of sensors, this embodiment having a single n-mode waveguide layer 620 on a substrate 610. Superstrates 630a, 630b..., in the form, for example, of chemically selective coatings (or selected to detect any desired property or having particular sensitivities, as previously noted) are deposited, or otherwise applied, on the waveguide layer. Each strip defines an interferometer channel. In this embodiment, light from a laser diode 605 is injected into waveguide layer 620 and is collimated by a waveguide lens 651. A mode selecting filter 655 can be provided to eliminate unwanted modes. As is known in the art, an optical grating can be used for this purpose (see e.g. R. Ulrich "Efficiency of Optical Grating Couplers", Journal of The Optical Society of America, Vol. 63, No. 11, 1973). Photodetectors 650 are provided, as in previous embodiments. In a form of this embodiment, each coating can exhibit a different absorbtivity, absorption, or reactivity to a specific chemical species and produces a spatially separated phase pattern at the output of the multichannel interferometer that is representative of a particular chemical species or class of chemicals. Thus, for example, by comparing the interferometer outputs with a library of reference standards, the chemical class or species maybe identified. Also, in all embodiments, small thickness changes in thin film thickness can appear as a refractive index change to a guiding beam, so a film thickness can be monitored.

As previously described, problems of temperature sensitivity of an interferometric sensor have been reduced by the devices and techniques set forth. However, the coating itself may exhibit a temperature dependence that could introduce error. This effect can be reduced by using adjacent channels with identical coatings, one protected from interaction with the local environment and the other exposed. This is shown, for example, in FIG. 7 in which identical strips 730a and 730b are deposited on waveguide layer 720, which is on substrate 710. The strip 730a is protected from chemical interaction with the environment by the protective superstrate or cover 770. The output signals from the interfering optical beams beneath the two strips can be substracted to remove the temperature dependence of the film strips 730a and 730b. A two branch interferometer (e.g. operated single mode) in a Mach-Zehnder configuration could also take advantage of this feature for example by providing identical chemically selective coatings (narrow hatching—FIGS. 8A and 8B) over each branch 881 and 882 (the branches preferably being of the same length) and protecting one of them from the environment with a protective superstrate. The superstrate is shown in broad hatching and, in the illustrated embodiment, covers most of the waveguide except the exposed coating.

The invention has been described with reference to particular preferred embodiments, but variations within the spirit and scope if the invention will occur to those skilled in the art. For example, it will be understood that in embodiments where a plurality of channels are used, one or more suitable light sources can be used or shared, and one or more suitable photodetectors can also be used or shared, for example on a multiplexed basis.

I claim:

1. A method for sensing a property of an environment, comprising the steps of:
   providing, in said environment, an optical waveguide layer between substrate and superstrate layers, said optical waveguide layer having a higher refractive index than the refractive indices of said substrate and superstrate;
   injecting a light beam into said waveguide such that at least two modes of said beam propagate in said waveguide, the effective index of refraction for said modes of said beam being affected by said property; and
   generating an electrical signal representative of the interfering product of said at least two modes of said beam which have propagated through said waveguide;
   said signal being indicative of said property of the evironment.

2. A method for sensing a substance in an environment, comprising the steps of:
   providing an optical waveguide having a boundary with an index of refraction that depends on said substance in the environment;
   injecting a light beam into said waveguide such that at least two modes of said beam propagate in said waveguide;
   generating an electrical signal representative of the interfering product of said at least two modes of said beam which have propagated through said waveguide;
   said signal being indicative of said substance.

3. The method as defined by claim 2, further comprising providing a coating at said boundary, said coating having an index of refraction that is affected by said substance.

4. The method as defined by claim 3, further comprising providing a plurality of said coatings at said boundary, said coatings having indices of refraction that are affected by said substance with different sensitivities.

5. The method as defined by claim 3, further comprising providing a plurality of said coatings at said boundary, said coatings having indices of refraction that are affected by different substances.

6. Apparatus for sensing a property of an environment, comprising:
   a susbtrate having an index of refraction $n_s$;
   a waveguide layer having a surface adjacent said substrate, said waveguide layer having an index of refraction $n_f$ that is greater than $n_s$;
   a superstrate adjacent the opposing surface of said waveguide layer, said superstrate having an index of refraction $n_c$ that is less than $n_f$, the index of refraction of said superstrate being affected by said environment;
   means for injecting an optical beam into said waveguide layer such that at least two modes of said beam propagate in said waveguide layer; and
   means for detecting the interfering product of said at least two modes of said beam which have propagated through said waveguide.

7. An apparatus as defined by claim 6 for sensing a substance in said environment, wherein said superstrate comprises a material whose index of refraction varies with said substance.

8. Apparatus as defined by claim 7, wherein said means for injecting an optical beam into said waveguide layer includes a source of coherent light and optical fiber means for coupling said coherent light to said waveguide layer.

9. Apparatus as defined by claim 8, wherein said means for detecting the beam output of said waveguide layer includes a photodetector and further fiber optical means to receive said optical beam output of said waveguide layer and couple said beam to said photodetector.

10. A sensing system comprising a plurality of sensing apparatuses as defined by claim 9, wherein the respective superstrate have different characteristics.

11. The sensing system as defined by claim 10, wherein said substrate comprise a common substrate and said waveguide layers comprise a common waveguide layer.

12. A sensing system comprising a plurality of sensing apparatuses as defined by claims 7, wherein the respective superstrate have different characteristics.

13. The sensing as defined by claim 12, wherein said substrate comprise a common substrate and said waveguide layers comprise a common waveguide layer.

14. Apparatus as defined by claim 6, wherein said means for injecting an optical beam into said waveguide layer includes a source of coherent light and optical fiber means for coupling said coherent light to said waveguide layer.

15. Apparatus as defined by claim 14, wherein said means for detecting the beam output of said waveguide layer includes a photodetector and further fiber optical means to receive said optical beam output of said waveguide layer and couple said beam to said photodetector.

16. A sensing system comprising a plurality of sensing apparatuses as defined by claim 6, wherein the respective superstrates have different characteristics.

17. The sensing system as defined by claim 16, wherein said substrate comprise a common substrate and said waveguide layers comprise a common waveguide layer.

18. Apparatus for sensing the presence of a substance in an environment, comprising:
   a pair of optical waveguide sections in said environment;
   a coating on each of said waveguide sections, each of said coatings having an index of refraction that changes when it is exposed to said substance;
   a protective covering on one of said coatings such that said one coating is protected from exposure to the environment and the other coating is exposed to said environment;
   means for injecting optical beams into said optical waveguide sections; and
   means responsive to the combined beam outputs for sensing said substance.

19. Apparatus as defined by claim 18, wherein said means responsive to the combined beam outputs comprises means for substracting the respective outputs of said optical waveguide sections.

* * * * *